United States Patent
Kruspe

(10) Patent No.: US 8,836,328 B2
(45) Date of Patent: Sep. 16, 2014

(54) ACOUSTIC EXCITATION WITH NMR PULSE

(75) Inventor: Thomas Kruspe, Wietzendorf (DE)

(73) Assignee: Baker Hughes Incorporated, Houston, TX (US)

( * ) Notice: Subject to any disclaimer, the term of this patent is extended or adjusted under 35 U.S.C. 154(b) by 317 days.

(21) Appl. No.: 13/018,595

(22) Filed: Feb. 1, 2011

(65) Prior Publication Data

US 2011/0187372 A1 Aug. 4, 2011

Related U.S. Application Data

(60) Provisional application No. 61/301,054, filed on Feb. 3, 2010.

(51) Int. Cl.
*G01V 3/00* (2006.01)
*G06F 19/00* (2011.01)
*G01V 3/32* (2006.01)
*G01N 24/08* (2006.01)

(52) U.S. Cl.
CPC .............. *G01N 24/081* (2013.01); *G01V 3/32* (2013.01)
USPC ........... 324/303; 324/306; 324/314; 324/333; 702/6

(58) Field of Classification Search
USPC ......................................... 324/303, 333, 314
See application file for complete search history.

(56) References Cited

U.S. PATENT DOCUMENTS

| | | | | |
|---|---|---|---|---|
| 2,615,956 A | * | 10/1952 | Broding | 324/333 |
| 2,702,559 A | * | 2/1955 | Bodine, Jr. | 137/38 |
| 2,757,738 A | * | 8/1956 | Ritchey | 166/248 |
| 3,048,773 A | * | 8/1962 | Brown | 324/303 |
| 3,227,228 A | * | 1/1966 | Bannister | 175/4 |
| 3,534,252 A | * | 10/1970 | Laukien | 324/314 |
| 4,453,219 A | * | 6/1984 | Clavier et al. | 702/10 |
| 4,717,878 A | * | 1/1988 | Taicher et al. | 324/303 |
| 4,901,018 A | * | 2/1990 | Lew | 324/306 |
| 5,291,137 A | * | 3/1994 | Freedman | 324/303 |
| 5,381,092 A | * | 1/1995 | Freedman | 324/303 |
| 5,432,446 A | * | 7/1995 | MacInnis et al. | 324/303 |
| 5,451,873 A | * | 9/1995 | Freedman et al. | 324/303 |
| 5,486,762 A | * | 1/1996 | Freedman et al. | 324/303 |
| 5,491,488 A | * | 2/1996 | Wu | 343/719 |
| 5,517,467 A | * | 5/1996 | Fromont et al. | 367/155 |
| 5,712,566 A | * | 1/1998 | Taicher et al. | 324/303 |
| 5,831,433 A | * | 11/1998 | Sezginer et al. | 324/303 |
| 6,023,164 A | * | 2/2000 | Prammer | 324/303 |
| 6,051,973 A | * | 4/2000 | Prammer | 324/303 |
| 6,107,797 A | * | 8/2000 | Sezginer | 324/303 |
| 6,163,153 A | | 12/2000 | Reiderman et al. | |
| 6,166,540 A | * | 12/2000 | Wollin | 324/300 |
| 6,184,681 B1 | * | 2/2001 | Heidler et al. | 324/303 |
| 6,246,236 B1 | * | 6/2001 | Poitzsch et al. | 324/303 |
| 6,255,818 B1 | * | 7/2001 | Heaton et al. | 324/303 |

(Continued)

FOREIGN PATENT DOCUMENTS

EP 256626 A2 * 2/1988 .............. G01V 1/053

*Primary Examiner* — Jermele M Hollington
*Assistant Examiner* — Christopher McAndrew
(74) *Attorney, Agent, or Firm* — Mossman Kumar & Tyler PC

(57) ABSTRACT

NMR measurements are made along with acoustic measurements using one tool. The antenna of the NMR sensor is used to create acoustic signals. Interference between the acoustic and NMR measurements is avoided due to the frequency difference, and by having the acoustic excitation during a wait time of the NMR pulse sequence.

19 Claims, 5 Drawing Sheets

(56) References Cited

U.S. PATENT DOCUMENTS

| | | | |
|---|---|---|---|
| 6,268,727 B1* | 7/2001 | King et al. | 324/306 |
| 6,326,785 B1 | 12/2001 | Kruspe | |
| 6,331,775 B1 | 12/2001 | Thern et al. | |
| 6,342,784 B1* | 1/2002 | Wollin | 324/303 |
| 6,411,087 B1* | 6/2002 | Fan et al. | 324/303 |
| 6,433,748 B1* | 8/2002 | Ekelund | 343/713 |
| 6,466,013 B1 | 10/2002 | Hawkes et al. | |
| 6,525,540 B1* | 2/2003 | Kong et al. | 324/338 |
| 6,545,471 B2* | 4/2003 | Wollin | 324/303 |
| 6,583,621 B2* | 6/2003 | Prammer et al. | 324/303 |
| 6,586,931 B2* | 7/2003 | Taicher | 324/303 |
| 6,650,114 B2 | 11/2003 | Kruspe et al. | |
| 6,691,779 B1* | 2/2004 | Sezginer et al. | 166/250.01 |
| 6,777,940 B2 | 8/2004 | Macune | |
| 6,815,950 B2* | 11/2004 | Speier | 324/303 |
| 6,825,659 B2* | 11/2004 | Prammer et al. | 324/303 |
| 6,831,571 B2* | 12/2004 | Bartel | 340/854.6 |
| 6,844,727 B2 | 1/2005 | Kruspe et al. | |
| 6,856,132 B2* | 2/2005 | Appel et al. | 324/303 |
| 6,891,376 B2* | 5/2005 | Hanstein et al. | 324/333 |
| 6,897,651 B2 | 5/2005 | Reiderman et al. | |
| 6,915,875 B2 | 7/2005 | Dubinsky et al. | |
| 6,958,610 B2* | 10/2005 | Gianzero | 324/342 |
| 7,009,707 B2* | 3/2006 | Beresford et al. | 356/478 |
| 7,017,822 B2* | 3/2006 | Aisenbrey | 235/487 |
| 7,046,165 B2* | 5/2006 | Beique et al. | 340/856.4 |
| 7,084,625 B2 | 8/2006 | Kruspe et al. | |
| 7,088,097 B2* | 8/2006 | Jeričevi | 324/303 |
| 7,126,333 B2 | 10/2006 | Beard et al. | |
| 7,148,693 B2* | 12/2006 | Ligneul et al. | 324/355 |
| 7,164,267 B2* | 1/2007 | Prammer et al. | 324/303 |
| 7,193,414 B2 | 3/2007 | Kruspe et al. | |
| 7,282,704 B2* | 10/2007 | Guo | 250/266 |
| 7,301,337 B2 | 11/2007 | Beard | |
| 7,348,781 B2* | 3/2008 | Tabanou et al. | 324/333 |
| 7,567,869 B2* | 7/2009 | Nikitenko et al. | 702/7 |
| 7,609,169 B2* | 10/2009 | Aiello | 340/854.3 |
| 7,839,149 B2* | 11/2010 | Wang et al. | 324/343 |
| 7,898,259 B2* | 3/2011 | Hall et al. | 324/339 |
| 7,913,756 B2* | 3/2011 | Kruspe | 166/248 |
| 8,049,508 B2* | 11/2011 | Gorek | 324/342 |
| 8,164,339 B2* | 4/2012 | Fang et al. | 324/356 |
| 8,278,928 B2* | 10/2012 | Bespalov | 324/326 |
| 8,344,726 B2* | 1/2013 | Romero | 324/303 |
| 2002/0167418 A1 | 11/2002 | Goswami et al. | |
| 2002/0171421 A1 | 11/2002 | Forgang et al. | |
| 2004/0020691 A1* | 2/2004 | Krueger | 175/27 |
| 2004/0155794 A1* | 8/2004 | Gardner | 340/855.7 |
| 2004/0257241 A1* | 12/2004 | Menger | 340/854.3 |
| 2006/0011385 A1* | 1/2006 | Seydoux et al. | 175/61 |
| 2008/0040042 A1* | 2/2008 | Page | 702/11 |
| 2008/0211507 A1* | 9/2008 | Zhdanov | 324/333 |
| 2008/0224705 A1* | 9/2008 | Simon et al. | 324/333 |
| 2008/0252295 A1* | 10/2008 | Pelegri et al. | 324/333 |
| 2008/0315882 A1* | 12/2008 | Seydoux et al. | 324/333 |
| 2009/0015253 A1* | 1/2009 | Forgang et al. | 324/303 |
| 2009/0072825 A1* | 3/2009 | Prammer et al. | 324/303 |
| 2009/0255669 A1* | 10/2009 | Ayan et al. | 166/250.15 |
| 2011/0109311 A1* | 5/2011 | Walsh | 324/309 |
| 2011/0234220 A1* | 9/2011 | Mitchell et al. | 324/303 |

\* cited by examiner

ACOUSTIC EXCITATION WITH NMR PULSE

CROSS-REFERENCES TO RELATED APPLICATIONS

This application claims priority from U.S. Provisional Patent Application Ser. No. 61/301,054 filed on Feb. 3, 2010.

BACKGROUND OF THE DISCLOSURE

1. Field of the Disclosure

The present disclosure is related to the field of downhole nuclear magnetic resonance (NMR) investigation of earth formations. In particular, the disclosure relates to an apparatus and method for methods for simultaneously making acoustic and Nuclear Magnetic Resonance measurements in a borehole of limited diameter.

2. Description of the Related Art

One of the most useful measurements of an earth formation made in measurement-while-drilling operations is that of porosity of the earth formation. The porosity is a measure of the hydrocarbon bearing capacity of the formation as more porous rocks have the capability of having more hydrocarbons.

Porosity measurements are commonly made using a neutron-porosity tool. Making measurements with a neutron-porosity tool requires the use of a nuclear source. In some applications, such as in drilling boreholes of small diameter (slimhole), space and safety considerations may preclude the use of a nuclear source. The term "slimhole" is defined in the Schlumberger Oilfield Glossary as:

An inexact term describing a borehole (and associated casing program) significantly smaller than a standard approach, commonly a wellbore less than 6 in. in diameter. The slimhole concept has its roots in the observed correlation between well costs and volume of rock extracted. If one can extract less rock, then well costs should fall. One form of slimhole work involves using more or less conventional equipment and procedures, but simply reducing the hole and casing sizes for each hole interval.

The present disclosure describes a tool capable of providing two independent estimates of formation porosity in a slimhole.

SUMMARY OF THE DISCLOSURE

One embodiment of the disclosure is an apparatus configured to evaluate an earth formation. The apparatus includes: a logging tool configured to be conveyed into a borehole; at least one antenna on a first sensor assembly on the logging tool, the at least one antenna configured to be switched between a transmit mode and a receive mode; at least one receiver amplifier on the first sensor assembly configured to produce an output responsive to a signal from the at least one antenna when in the receive mode, the signal being one of: (i) a radio frequency (RF) signal, and (ii) an acoustic frequency (AF) signal; and at least one processor configured to estimate from the output of the at least one receiver amplifier a property of the earth formation.

Another embodiment of the disclosure is a method of evaluating an earth formation. The method includes: conveying a logging tool configured to be conveyed into a borehole; switching at least one antenna on a first sensor assembly on the logging tool to a receive mode; activating an antenna on a second sensor assembly for generating a first signal that is one of: (i) a radio frequency (RF) signal, and (ii) an acoustic frequency (AF) signal; using the at least one antenna on the first sensor assembly to provide a second signal responsive to the first signal; using at least one receiver amplifier on the first sensor assembly to produce an output responsive to the second signal; and using at least one processor for estimating from the output of the at least one receiver amplifier a property of the earth formation.

Another embodiment of the disclosure is a computer-readable medium having stored thereon instructions that when read by at least one processor enable the at least one processor to execute a method. The method includes: switching at least one antenna on a first sensor assembly on a logging tool conveyed in a borehole to a receive mode; activating an antenna on a second sensor assembly for generating a first signal that is one of: (i) a radio frequency (RF) signal, and (ii) an audio frequency (AF) signal; using the at least one antenna on the first sensor assembly to provide a second signal responsive to the first signal; using at least one receiver amplifier on the first sensor assembly to produce an output responsive to the second signal; and using at least one processor for estimating from the output of the at least one receiver amplifier a property of the earth formation.

BRIEF DESCRIPTION OF THE DRAWINGS

The present disclosure is best understood with reference to the accompanying figures in which like numerals refer to like elements, and in which.

DETAILED DESCRIPTION OF THE DISCLOSURE

Figure 1:
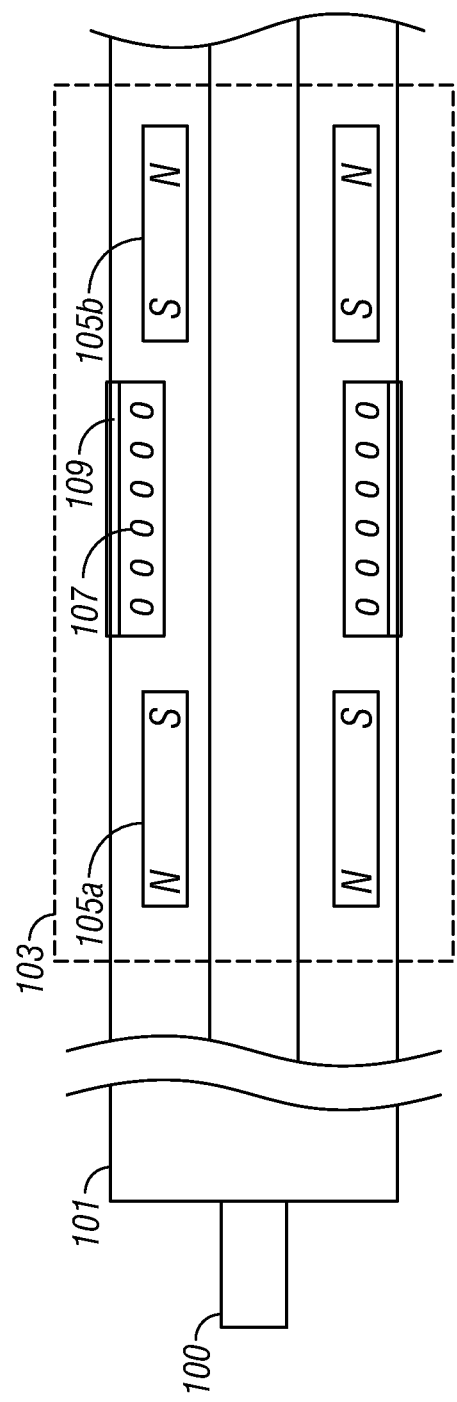
FIG. 1 shows a sensor module of the present disclosure.

The present disclosure is directed towards a logging tool configured to make simultaneous NMR measurements and acoustic measurements in a borehole. FIG. 1 shows a sensor module 103 on a bottomhole assembly 101. The BHA may be conveyed downhole on a coiled tubing 100. The sensor assembly 103 includes a magnet arrangement comprising opposed magnets 105a, 105b that produces a region of examination in the earth formation between the two magnets. It should be noted that the use of coiled tubing is not to be construed as a limitation and that the apparatus may also be deployed on a wireline or on a bottomhole assembly conveyed on a drillstring.

The sensor assembly also includes an antenna 107. In the present disclosure, the antenna 107 may be used as a transmitter antenna or as a receiver antenna. This is discussed further below. As would be known to those versed in the art, the antenna is typically pulsed with a radio-frequency (RF) pulse sequence of the form:

$$[W_i - 180_x - t_i - 90_x - (t_{cp} - 180_y - t_{cp} - \text{echo})_j]_i \quad (1)$$

where j=1, 2, ..., J, and J is the number of echoes collected in a single CPMG sequence, where i=1, 2, ..., I and I is the number of waiting times used in the pulse sequence, where $W_i$ are the recovery times before the inversion pulse, and where $t_i$ are the recovery times before a CPMG sequence, and where $t_{CP}$ is the Can-Purcell spacing. The phase of the RF pulses 90 and 180 is denoted by the subscripts X and Y, Y being phase shifted by $\pi/2$ radians with respect to X. The subscripts also conventionally relate to the axis about which rotation of the magnetization occurs during the RF pulse in a local Cartesian coordinate system centered on the nucleus in which the static magnetic field is aligned in the Z direction and the RF field in the X direction. This sequence can be used to measure both T1 and T2, but is very time consuming, limiting logging speed. If $t_{CP}$ is set to zero and the inverting pulse is omitted then the sequence defaults to standard CPMG for measuring T2 only. U.S. Pat. No. 6,466,013 to Hawkes et al., and U.S. Pat. No. 6,163,153 to Reiderman et al. teach use of a modified CPMG sequence in which the refocusing pulses have a tipping angle less than 180°. With such a modified CPMG sequence, power usage is reduced without a significant reduction in the signal to noise ratio (SNR). This gives a pulse sequence of the form:

$$[W_i-180_x-t_i-T_x-(t_{cp}-R_y-t_{cp}-\text{echo})_j]_i$$

where j=1, 2, . . . , J, and J is the number of echoes collected in a single CPMG sequence, where i=1, 2, . . . , I and I is the number of waiting times used in the pulse sequence, where $W_i$ are the recovery times before the inversion pulse, and where $t_i$ are the recovery times before a CPMG sequence, $t_{CP}$ is the Carr-Purcell spacing, T is a tipping pulse and R is a refocusing pulse.

In the present disclosure, the antenna 107 of the NMR sensor is also used to produce acoustic pulses for making acoustic measurements. In one embodiment, the Lorenzian force created by eddy currents induced in the conductive environment of the formation are used to create acoustic pulses. In another embodiment, magnetostrictive elements are provided in the tool 103 that are excited by the transmitter antenna.

In yet another embodiment the Lorenzian forces of the current in the Antenna windings create a local deformation of the area around the antenna and forcing acoustic signals into the geologic formation.

The antenna 107 is embedded in elastic material 109 to make it sensitive to acoustic frequencies in a relatively low frequency range. When the antenna 107 vibrates due to acoustic waves in the presence of the magnetic field produced by the magnets 105a, 105b, electrical signals are produced responsive to the acoustic waves.

Figure 2A:
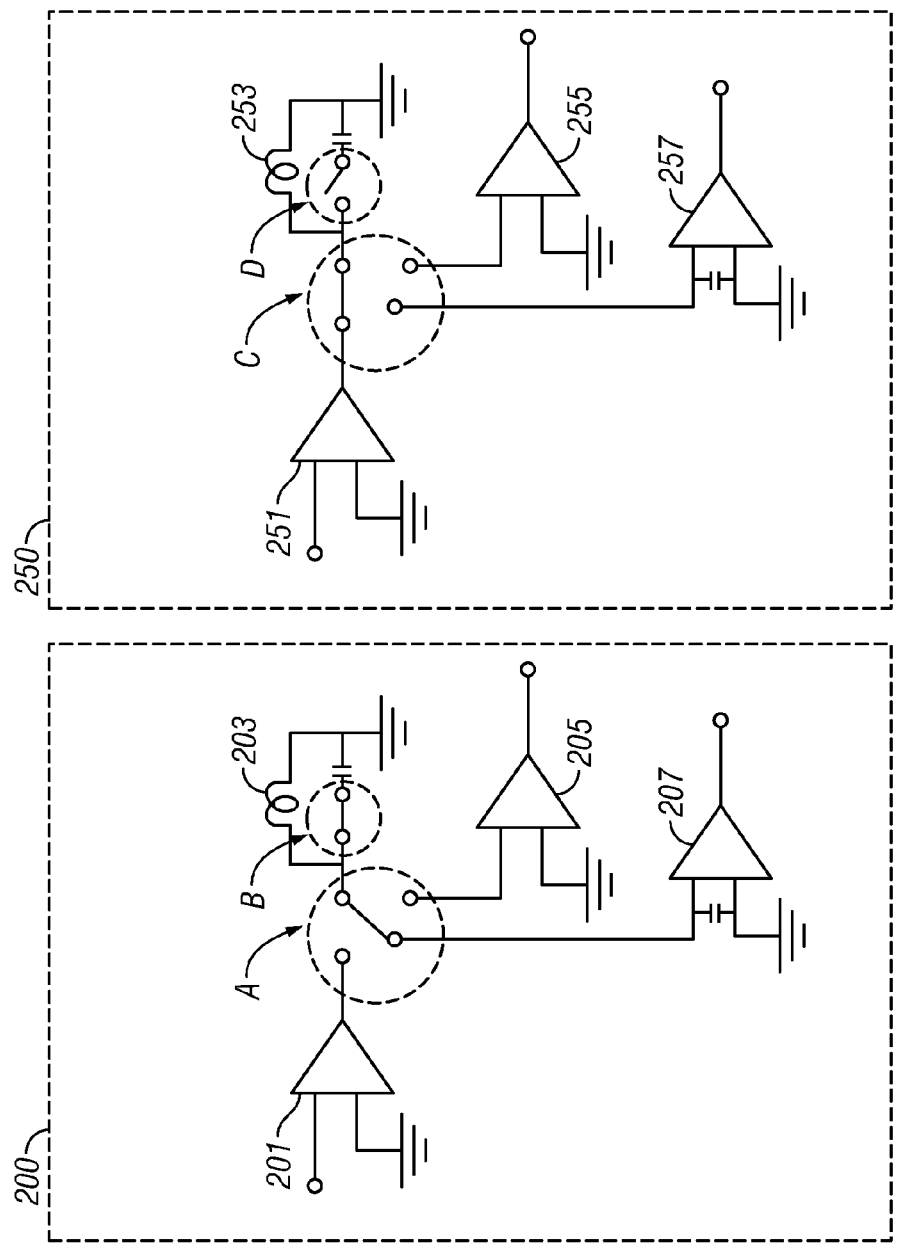
FIGS. 2a, 2b show a circuit diagram of an apparatus suitable for carrying out the method of the present disclosure.
Figure 2B:
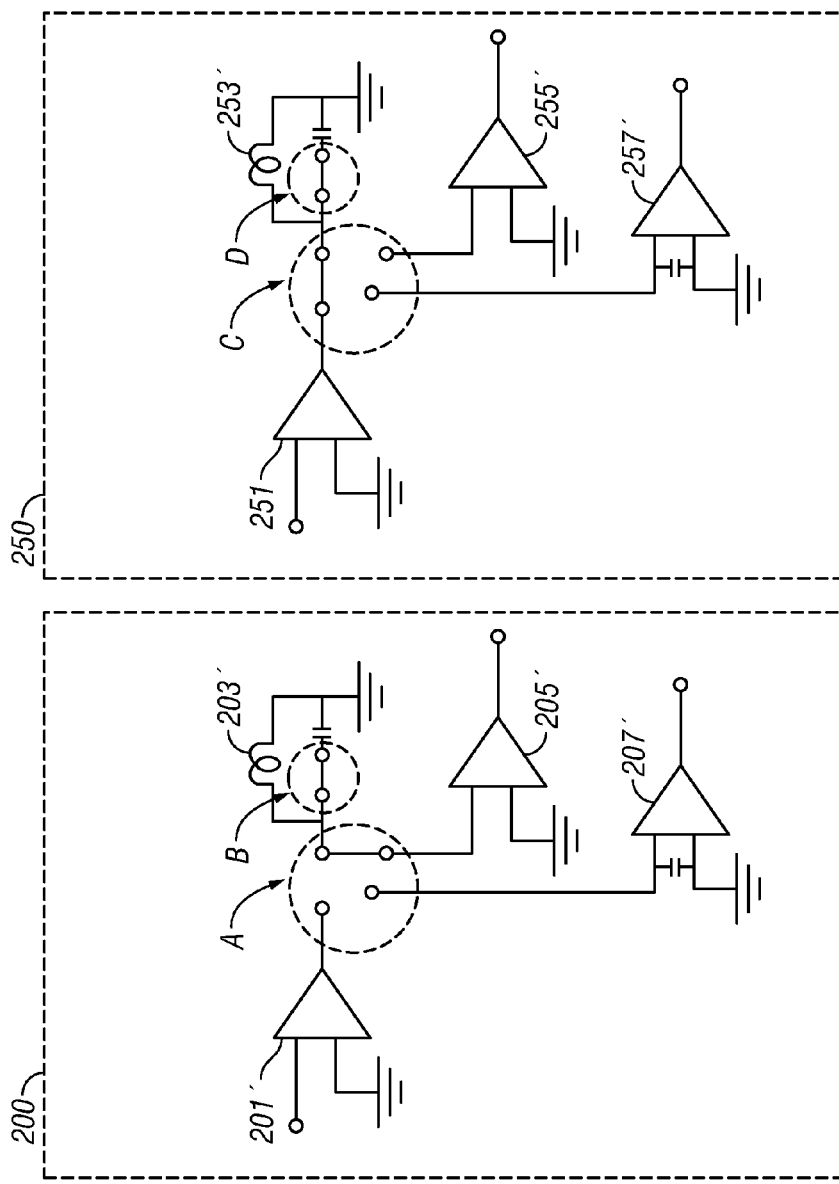

Turning now to FIGS. 2a, 2b, the method of the present disclosure is illustrated. The logging tool is provided with two sensor modules 200, 250 having the structure of the sensor module 103 of FIG. 1. The modules 200, 250 are each provided with a transmitter amplifier 201, 251; NMR receiver amplifiers 205, 255; and acoustic receiver amplifiers 207, 257. The term "NMR receiver amplifier" refers to an RF amplifier responsive to RF signals and the term "acoustic receiver amplifier" refers to an amplifier that operates in the acoustic frequency range (typically 200 Hz to 10 kHz).

In FIG. 2a, the antenna 253 acts as a transmitter antenna (note the position of switch C connecting the antenna 253 to the transmitter amplifier 251. With the switch D in the indicated position, the antenna circuit 253 is tuned to the selected NMR-frequency. With switch D in open-position the transmitter antenna is not tuned and can operate in the acoustic frequency range w/o interference with the NMR spin system. The NMR receiver amplifier 255 and the acoustic receiver amplifier 257 are disconnected. The antenna 203 acts as an acoustic microphone: note the position of switch A which disconnects the transmitter amplifier 201 and connects the acoustic receiver amplifier 207 to antenna 203. Note also the position of the switch B which reduces the tuning frequency of the circuitry. As noted above, the antenna 203 will receive signals in the acoustic range due to acoustic waves produced by the antenna 253 in the transmit mode as the antenna is in the magnetic field produced by magnets. See 105a, 105b.

In FIG. 2b, switch C is in the same position as in FIG. 2a, so that 253' acts as a NMR transmitter antenna and receiver amplifiers 255' and 257' are disconnected. Switch D is closed, so the antenna 253' is tuned to NMR frequency for the receiver—(200) and transmitter—case (250). However, switch A is now positioned to connect the antenna 203' to the NMR receiver amplifier 205' and the acoustic receiver amplifier 207' is disconnected. In this configuration, and with the switch B closed, the NMR receiver amplifier receives NMR signals as in conventional NMR tools. Those versed in the art would also recognize the possibility of operating switch C in FIG. 2a so that, in addition to using the antenna 253 for generating pulses, the switch C is also connected to NMR receiver amplifier 255 to receive spin echo signals resulting from the pulses. The needed rapid switching is feasible in small size tools with reduced antenna inductance. Both antennas can operate in parallel switching between transmit and receive mode according to the NMR measurement sequence. Having both antennas working in parallel would minimize unwanted interferences.

The converse situation in which sensor assembly 200 is used as a transmitter (by connecting transmitter antenna 201 to the antenna 203 by suitable positioning of switch A) and the sensor assembly 250 is used as a receiver is easily comprehended. With such an arrangement, acoustic signals are recorded with opposite directions of propagation, something that is known to be desirable for borehole compensation. The term "borehole compensation" refers to a method in which correction is made for changes in the borehole diameter. It should further be noted that while the switches A, B, C, D are indicated as mechanical switches, they would likely be implemented as electronic switches controlled by a processor. It should also be noted that each of the sensor modules 200 and 250 has been shown with only one antenna. This is not to be construed as a limitation. Each sensor module may be provided with two antennas: one of which is used as a transmitter and the other is used as a receiver. Appropriate modification to the switches would be apparent to those skilled in the art.

Figure 3:
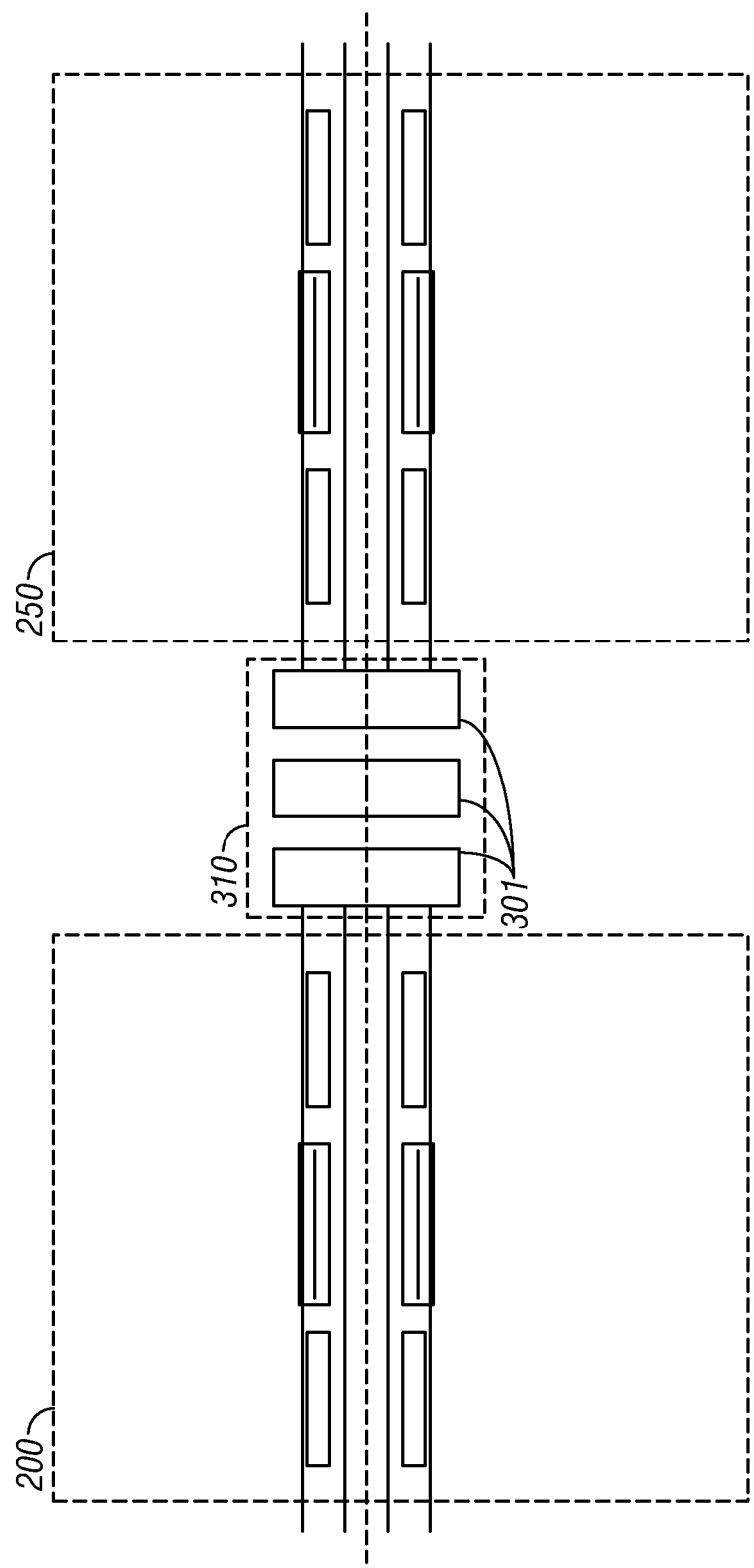
FIG. 3 shows two sensor modules separated by an acoustic attenuator.

In order to attenuate acoustic signals that are propagating directly through the BHA, the sensor assemblies 200, 250 are separated by an attenuator section. As shown in FIG. 3, the attenuator section 310 may comprise a series of mass irregularities such as rings 301. Such an arrangement is disclosed in U.S. Pat. No. 6,915,875 to Dubinsky et al., having the same assignee as the present disclosure and the contents of which are incorporated herein by reference.

As noted in U.S. Pat. No. 6,650,114 to Kruspe et al, having the same assignee as the present disclosure and the contents of which are incorporated herein by reference, using a variable interecho time, it is possible to estimate to the total porosity, clay bound water and effective porosity. Alternatively, by using a fixed interecho time, a subset of total porosity, clay bound water and effective porosity can be estimated.

In order to reduce the total acquisition time, instead of generating RF and acoustic signals sequentially, use is made of the wait time for the CPMG (or modified CPMG) sequence. The acoustic signals are produced during the wait time W, so that the total acquisition time is no more than for just NMR logging alone. The acoustic signal is in a frequency range that is much lower than the RF frequency (and the Larmor frequency of the nuclear spins). Consequently, the acoustic signal does not affect the recovery of nuclear spins during the wait time.

Figure 4:
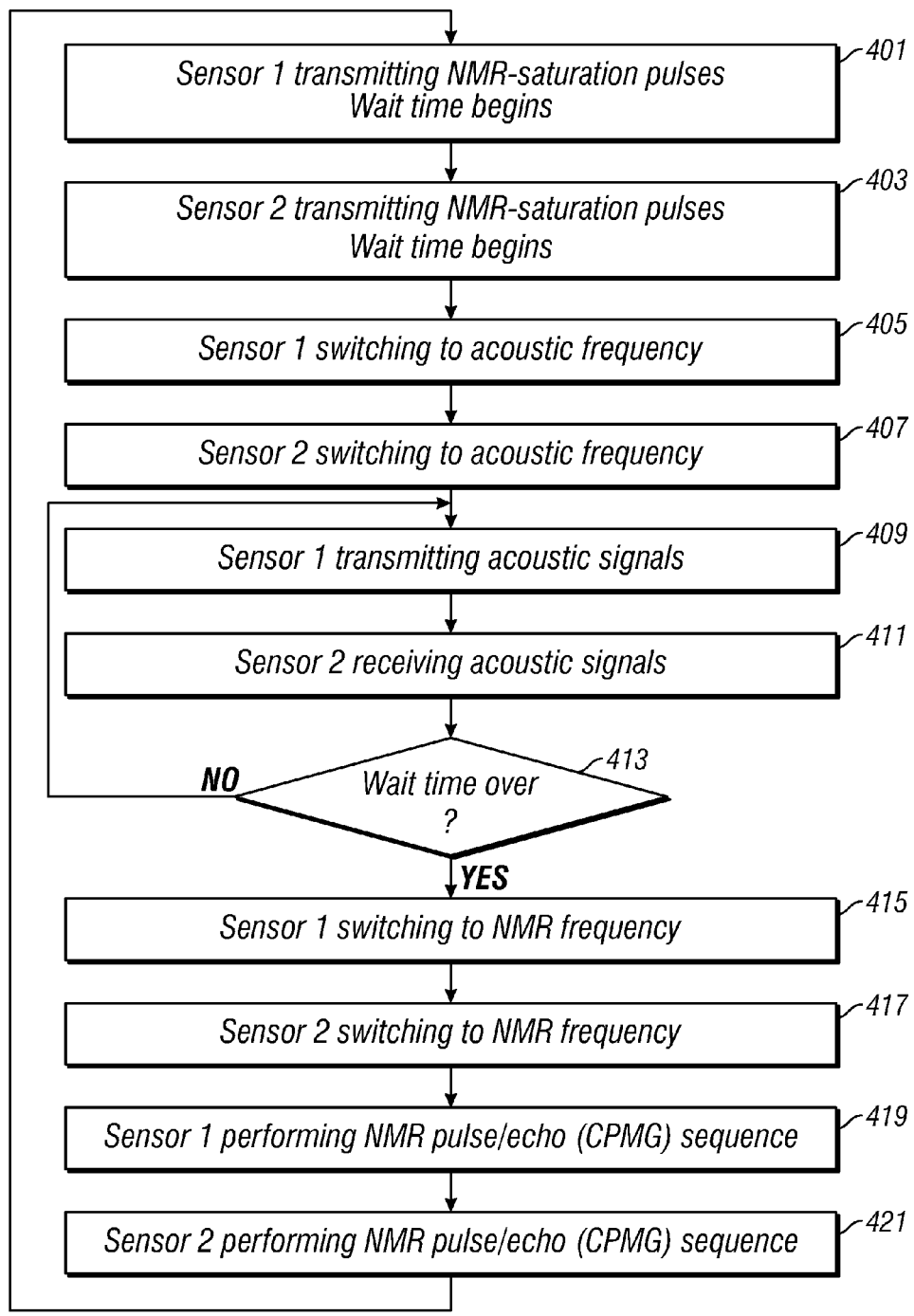
FIG. 4 shows an exemplary flow chart of the manner of data acquisition with the present method.

FIG. 4 shows a flow chart of an exemplary method of data acquisition. Sensors 1 and 2 (200, 250) transmit saturation pulses to saturate nuclear spins in their corresponding regions of evaluation 401, 403. Sensors 200, 250 switch to acoustic frequencies 405, 407 and transmit acoustic signals 409, 411 that are acquired by the acoustic receiver amplifiers 207, 257. A check is made 413 to see if the wait time is over 413. If the wait time is not over, additional acoustic signals are acquired. If the wait time is over, the sensors 200, 250 switch to the NMR frequency 415, 417 and NMR pulse echo signals are acquired 419, 421.

The acoustic velocity estimation is based on the distance between the acoustic source and the receiver antenna and the travel time for the acoustic signal. In order to reduce the uncertainty in velocity, the acoustic source should be as small as possible and use a magnetostrictive element with a high magnetostrictive coefficient. Ferrites F47 and F44 from vendor NMG-Neosid show positive magnetostriction. The F47 and F44 Ferrites are Manganese Zink Ferrites.

The acoustic velocities determined in this fashion can be used to provide an estimate of the porosity using, for example, the Wylie time average equation. Additionally, the density of the formation may be estimated using the Gardner, Gardner & Gregory relation:

$$\rho_b = 0.23 V_p^{0.25}.$$

The advantages of the method and apparatus described above would be clear. First and foremost, NMR and acoustic measurements can be made with the same logging tool, the tool having a length about the same as an acoustic logging tool. Secondly, acquisition of NMR and acoustic signals can be made in the same time as that needed for NMR signals only. Thirdly, the logging tool can be used in slimhole applications for porosity determination where conventional nuclear porosity tools cannot be used.

As is standard practice in well-logging, the results of the processing are recorded on a suitable medium. Implicit in the processing of the data is the use of a computer program implemented on a suitable machine-readable medium that enables a processor to perform the control and processing. The machine readable medium may include ROMs, EPROMs, EAROMs, Flash Memories and Optical disks. The examples of a machine-readable medium given here are all non-transitory media. The processor may be on the BHA or at a surface location.

While the foregoing disclosure is directed to the preferred embodiments of the disclosure, various modifications will be apparent to those skilled in the art. It is intended that all such variations within the scope and spirit of the appended claims be embraced by the foregoing disclosure.

What is claimed is:

1. An apparatus configured to evaluate an earth formation, the apparatus comprising:
    a logging tool configured to be conveyed into a borehole;
    a first antenna on a first sensor assembly on the logging tool, the first antenna configured to be switched between a transmit mode and a receive mode, the first antenna configured to be switched between being tuned to a radio frequency signal and an acoustic frequency signal;
    at least one receiver amplifier on the first sensor assembly configured to produce a first output responsive to the radio frequency signal from the first antenna when in the receive mode and tuned to the radio frequency signal, the at least one receiver amplifier on the first sensor assembly configured to produce a second output responsive to the audio frequency signal from the first antenna when in the receive mode and tuned to the audio frequency signal; and
    at least one processor configured to estimate from the first and second outputs of the at least one receiver amplifier a property of the earth formation.

2. The apparatus of claim 1 further comprising a plurality of antennas, wherein the at least one receiver amplifier is configured to produce an output responsive to each signal of a plurality of signals from each of the plurality of antennas, wherein the plurality of signals from each antenna of the plurality of antennas include at least (i) a radio frequency (RF) signal, and (ii) an audio frequency (AF) signal.

3. The apparatus of claim 1 wherein the processor is at a location selected from: (i) a downhole location, or (ii) a surface location.

4. The apparatus of claim 1, further comprising:
    a second antenna on a second sensor assembly on the logging tool, the second antenna configured to be switched between a transmit mode and a receive mode and configured to be switched between generating a radio frequency signal and an acoustic frequency signal; and
    wherein the first antenna is configured to be switched between the transmit mode and the receive mode when the second antenna is switched between the transmit mode and the receive mode.

5. The apparatus of claim 4 wherein the first is responsive to an excitation of the second antenna.

6. The apparatus of claim 4 wherein the first and second antennas are embedded in an elastic material configured to be sensitive to an acoustic frequency of the acoustic frequency signals.

7. The apparatus of claim 4 wherein the second sensor assembly further comprises a magnet arrangement to enable generation of spin echo signals in the earth formation when the second antenna is in the transmit mode and generating the radio frequency signal.

8. The apparatus of claim 7 wherein the at least one processor is further configured to pulse the second antenna using a pulse sequence of the form:

$$[W_i - 180_x - t_i - T_x - (t_{cp} - R_y - t_{cp} - \text{echo})_j]_i$$

where j=1, 2, . . . , J, and J is the number of echoes collected in a single CPMG sequence, where i=1, 2, . . . , I and I is the number of waiting times used in the pulse sequence, where $W_i$ are the recovery times before the inversion pulse, and where $t_i$ are the recovery times before a CPMG sequence, $t_{CP}$ is the Carr-Purcell spacing, T is a tipping pulse and R is a refocusing pulse.

9. The apparatus of claim 8 wherein the second antenna is further configured to generate the audio frequency signal during a wait time W of the pulse sequence.

10. The apparatus of claim 1 further comprising a coiled tubing configured to convey the logging tool into the borehole.

11. A method of evaluating an earth formation, the method comprising:
    conveying a logging tool configured into a borehole;
    switching an antenna on a first sensor assembly on the logging tool to a receive mode;
    activating an antenna on a second sensor assembly for generating a first signal;
    using the antenna on the first sensor assembly to provide a second signal responsive to the first signal, the second signal being a radio frequency (RF) signal;

using at least one receiver amplifier on the first sensor assembly to produce an output responsive to the second signal;

activating the antenna on the second sensor assembly for generating an acoustic signal;

using the antenna on the first sensor assembly to provide an audio frequency (AF) signal responsive to the acoustic signal;

using the at least one receiver amplifier on the first sensor assembly to produce an output responsive to the AF signal; and using at least one processor for estimating from the output of the at least one receiver amplifier a property of the earth formation.

12. The method of claim 11 further comprising using a plurality of antennas, wherein the at least one receiver amplifier is configured to produce an output responsive to each signal of a plurality of signals from each of the plurality of antennas, wherein the plurality of signals from each antenna of the plurality of antennas include at least (i) a radio frequency (RF) signal, and (ii) an audio frequency (AF) signal.

13. The method of claim 11 further comprising positioning the at least one processor at a location selected from: (i) a downhole location, and (ii) a surface location.

14. The method of claim 11 wherein first signal further comprises spin echo signals in the earth formation.

15. The method of claim 14 wherein generating the spin echo signals further comprises pulsing the antenna on the second sensor assembly using a pulse sequence of the form:

$$[W_i-180_x-t_i-T_x-(t_{cp}-R_y-t_{cp}-\text{echo})_j]_i$$

where j=1, 2, ..., J, and J is the number of echoes collected in a single CPMG sequence, where i=1, 2, ..., I and I is the number of waiting times used in the pulse sequence, where $W_i$ are the recovery times before the inversion pulse, and where $t_i$ are the recovery times before a CPMG sequence, $t_{CP}$ is the Carr-Purcell spacing, T is a tipping pulse and R is a refocusing pulse.

16. The method of claim 15 wherein activating the antenna on the second sensor assembly for generating the acoustic signal further comprises activating the antenna on the second assembly for generating a signal in the AF range during a wait time W.

17. The method of claim 11 further comprising using a coiled tubing for conveying the logging tool into the borehole.

18. A non-transitory computer-readable medium having stored thereon instructions that when read by at least one processor enable the at least one processor to execute a method, the method comprising:

switching antenna on a first sensor assembly on a logging tool conveyed in a borehole to a receive mode;

activating an antenna on a second sensor assembly for generating a first signal;

using the antenna on the first sensor assembly to provide a second signal responsive to the first signal, the second signal being a radio frequency (RF) signal;

using at least one receiver amplifier on the first sensor assembly to produce an output responsive to the second signal;

activating the antenna on the second sensor assembly for generating an acoustic signal;

using the antenna on the first sensor assembly to provide an audio frequency (AF) signal responsive to the acoustic signal;

using the at least one receiver amplifier on the first sensor assembly to produce an output responsive to the fourth signal; and using at least one processor for estimating from the output of the at least one receiver amplifier a property of the earth formation.

19. The non-transitory computer-readable medium of claim 18 further comprising at least one of: (i) a ROMs, (ii) an EPROM, (iii) an EAROM, (iv) a flash memory, or (v) an optical disk.

* * * * *